United States Patent [19]

Thompson et al.

[11] Patent Number: 5,002,069
[45] Date of Patent: Mar. 26, 1991

[54] ADJUSTABLE FLUID CONTROL POUCH

[75] Inventors: Joseph F. Thompson, Lindenhurst, Ill.; Mary Coyne, Redwood, Calif.

[73] Assignee: Baxter International, Inc., Deerfield, Ill.

[21] Appl. No.: 516,372

[22] Filed: Apr. 30, 1990

[51] Int. Cl.⁵ .............................................. A61B 19/00
[52] U.S. Cl. .................................... 128/849; 128/853; 604/356
[58] Field of Search ............................... 128/849–855; 604/353–357

[56] References Cited

U.S. PATENT DOCUMENTS

| | | | |
|---|---|---|---|
| 3,103,930 | 9/1963 | Collett et al. | 604/355 |
| 3,244,169 | 4/1966 | Baxter | 128/850 |
| 3,364,928 | 1/1968 | Creager, Jr. et al. | |
| 3,386,444 | 6/1968 | Brenner et al. | 604/357 |
| 3,791,382 | 2/1974 | Collins | |
| 4,051,845 | 10/1977 | Collins | |
| 4,076,017 | 2/1978 | Haswell | 128/849 |
| 4,105,019 | 8/1978 | Haswell | |
| 4,149,537 | 4/1979 | Haswell | |
| 4,439,720 | 12/1984 | Morris et al. | |
| 4,462,396 | 7/1984 | Wichman | 128/853 |
| 4,476,860 | 10/1984 | Collins | |
| 4,559,937 | 12/1985 | Vinson | |
| 4,570,628 | 2/1986 | Neal | |
| 4,598,458 | 7/1986 | McAllester | |
| 4,869,271 | 9/1989 | Idris | 128/853 |
| 4,890,628 | 1/1990 | Jackson | 128/849 |

FOREIGN PATENT DOCUMENTS 0182766 5/1986 European Pat. Off. ............ 128/849

OTHER PUBLICATIONS

Neurological Drape with Pouch-Baxter Healthcare Corp.-1988.
Arthroscopy Packs-Baxter Healthcare Corp.-1989.
Cesarean Birth Packs-Baxter Healthcare Corp.-1988.

Primary Examiner—Robert A. Hafer
Assistant Examiner—Kerry Owens
Attorney, Agent, or Firm—Kay H. Pierce; Paul C. Flattery

[57] ABSTRACT

A surgical drape is described which includes a pouch having a drawstring through a channel which runs along one edge of the pouch. When the drawstring is pulled through the channel, the edge of the pouch can be gathered to create a concave surface to control and contain fluids about a surgical site.

16 Claims, 8 Drawing Sheets

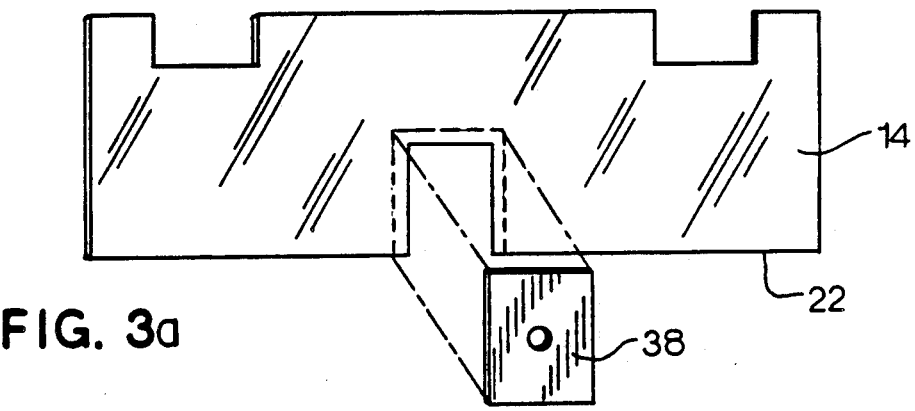
FIG. 3a
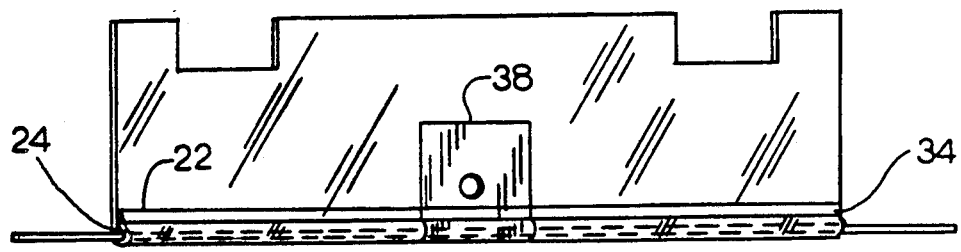
FIG. 3b
FIG. 3c
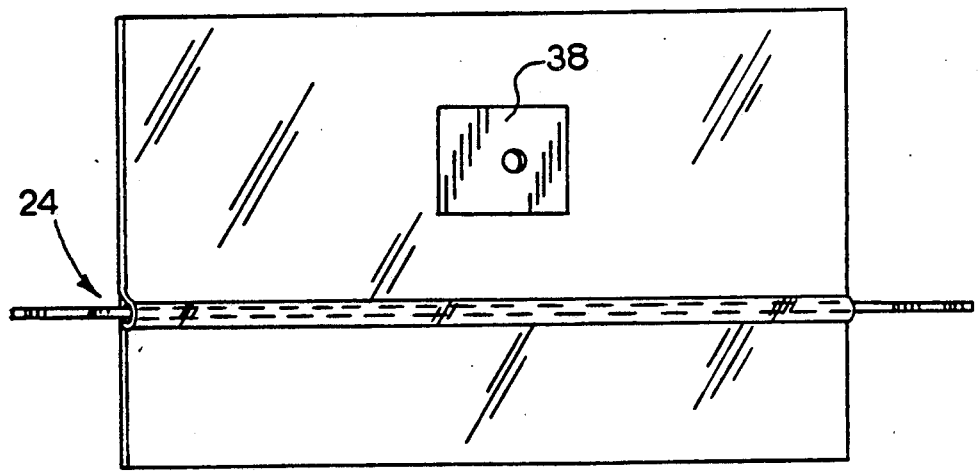

ADJUSTABLE FLUID CONTROL POUCH

BACKGROUND OF THE INVENTION

The present invention relates to a surgical drape which includes a pouch for fluid containment for channelling and collecting fluids at a surgical site during an operation.

During many surgical procedures, it is frequently desirable to create a sterile field around a surgical site to reduce the possibility of infection of a patient. Typically, a sterile field is created by draping a sterile material over a patient in such a manner as to leave an opening only at the actual site of an incision. Such surgical drapes have been used for many years. Originally the focus of draping was to protect the patient from infection. Recently, that focus has expanded to include protection of the staff from infection. Examples of types of infection that a surgical staff member may be exposed to from fluids include the hepatitis B virus and the AIDS virus. Thus, another function of surgical drapes used today is to provide a barrier to the penetration of liquids or bacteria which may result in contamination of the patient or the staff performing the surgical procedure.

In some surgical procedures very large volumes of fluid may be present either from irrigation sources or from the patient's body fluids. It is desirable in most instances to control and contain such fluids. Some drapes have been used in the past which contain a pouch to collect fluids present during surgery.

One of the disadvantages of the currently available drapes with pouches is that they are relatively difficult to manipulate into the form of an open pouch. Once formed, the pouch can also be difficult to maintain in a fixed position away from a drape to which it is attached. It is important to maintain the pouch away from the drape to allow fluids to flow into the pouch (as opposed to flowing around or over the pouch and onto the drape). Another disadvantage of pouches previously used is that they generally lacked a satisfactory mechanism for maintaining the pouch in a patient-specific shape or configuration. Therefore, a need existed to provide a drape which includes a pouch that can be both arranged in a variety of patient-specific shapes and maintained in a such a specific shape away from the drape throughout a surgical procedure without undue or repeated manipulation by members of the surgical staff.

Another requirement of a drape containing a pouch is that prior to use of the drape, it is necessary to be able to fold the drape in a compact manner for storage and for ease of placement over a patient using sterile techniques prior to beginning a surgical procedure. Therefore, it is necessary for any pouch which may be attached to a surgical drape to be able to be folded to lie flat against a drape prior to use. Conversely, while the drape and pouch are in use, it is highly desirable for the pouch to form a concave surface which extends away from the drape and can be easily maintained in a position away from the drape throughout a surgical procedure.

SUMMARY OF THE INVENTION

In view of the foregoing, it is an object of the invention to provide a pouch which can be arranged to form a variety of shapes immediately before or during a surgical procedure and to maintain such shape without further manipulation by members of the surgical staff.

It is yet another object of the invention to provide a pouch which can be used with a surgical drape that can be folded flat against the drape prior to use and can be maintained away from the drape during use.

Finally, it is an object of the invention to provide a pouch for use in surgical procedures to control and direct fluid flow and to catch and hold articles such as sponges and instruments in which the pouch is relatively inexpensive and simple to manufacture.

Each of the objects described above, as well as other objects which will become obvious from the following description, is achieved through the use of a pouch that is formed of at least one sheet of a flexible, fluid-impervious material. The sheet has a front surface, a back surface, a first edge for placement in close proximity to a surgical site, and a second edge located away from a first edge. At least one channel is provided in the sheet along a portion of the second edge. A drawstring is provided which extends through at least a portion of the channel. The drawstring has at least one end that extends beyond the channel. The end of the drawstring which extends beyond the channel can be pulled so as to gather at least a portion of the second edge of the sheet to form a generally concave surface that is patient-specific in shape. This concave surface can control and contain fluids that are present at the surgical site.

In one embodiment of the invention, the pouch is attached to a surgical drape having an opening therethrough so that the first edge of the sheet of the pouch is in close proximity to the opening in the drape. The second edge which is gathered during use of the pouch is located away from the opening to form a concave surface between the first and second edges that is used to control fluids.

BRIEF DESCRIPTION OF THE DRAWINGS

FIGS. 3(a), (b) and (c) are plan views of various embodiments of the invention as shown during a portion of the manufacturing phase in which a channel is formed;

DETAILED DESCRIPTION OF THE PREFERRED EMBODIMENT

Figure 1:
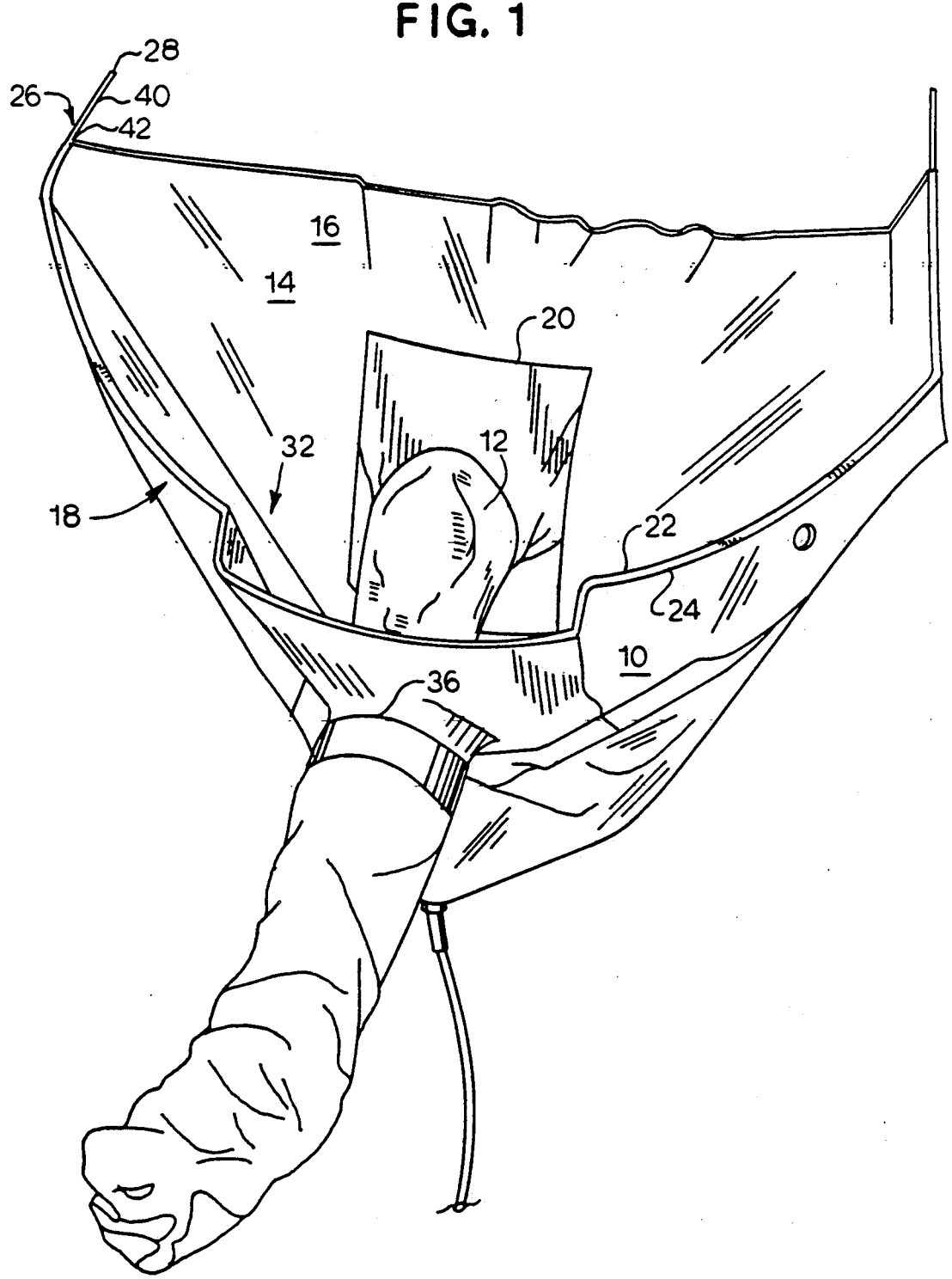
FIG. 1 is a perspective view of the preferred embodiment of the invention when the pouch is in the open position prior to gathering.

In the preferred embodiment of the invention, a pouch 10 for controlling fluids at a surgical site 12 is provided. The pouch is formed from at least one sheet of a flexible, fluid impervious material 14. The sheet has a front surface 16 and a back surface 18. The sheet includes a first edge 20 for placement in close proximity to the surgical site 12. A second edge 22 is located away from the first edge. The second edge includes at least one channel 24 which extends along at least a portion of the second edge 22. In the preferred embodiment of the invention, a drawstring 26 is provided which has first and second ends 28 and 30, respectively. The drawstring extends through at least a portion of the channel 24 to allow the drawstring to be pulled so as to gather at least a portion of the second edge 22 along the channel to form a generally concave surface 32. The purpose of the concave surface is to control fluids at the surgical site 12 and to contain such fluids.

Figure 2:
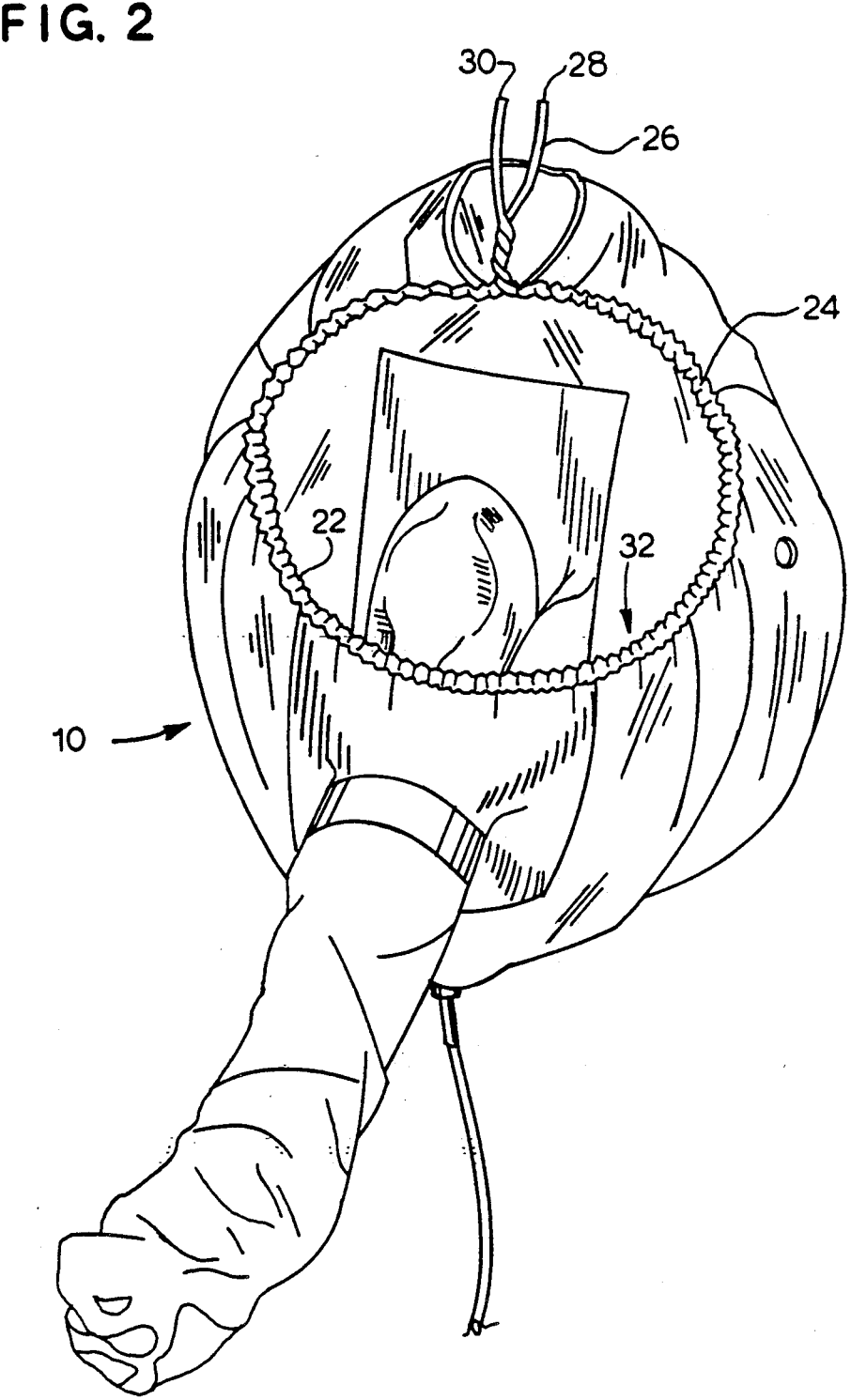
FIG. 2 is a perspective view of the preferred embodiment of the invention with the pouch gathered to form a concave surface about the surgical site.

Referring now to FIG. 2, in the preferred embodiment of the invention, the drawstring has ends 28 and 30 which each extend beyond opposite ends of the channel 24. This allows both ends 28, 30 of the drawstring 26 to be pulled to gather the second edge 22 of the pouch 10. As can be seen in FIG. 2 in the preferred embodiment of the invention, a means for securing the drawstrings can be provided. In this embodiment, after the ends 28, 30 of the drawstring 26 have been pulled, the ends are twisted about one another to secure them into a fixed position. This allows the concave surface 32 which is formed by gathering the second edge 22 to be maintained in a relatively fixed position throughout a surgical procedure without undue or repeated manipulation by the surgical staff.

In general, the pouch may be formed from a variety of materials. In the preferred embodiment, however, the pouch is formed from a transparent flexible material which does not allow liquid to pass therethrough. Examples of such materials include a variety of polymeric films such as polyethylene, polypropylene, polyester, polyvinylchloride, or a combination thereof. Another desirable feature of the material chosen to form the pouch is that it be sealable to itself through the use of heat or ultrasonic sealing techniques or that it be capable of forming a seam through the use of an adhesive.

In other embodiments, the pouch may be formed from an opaque material or may include gradations on a portion of the pouch to measure the amount of fluid that is captured in the pouch.

In one embodiment of the invention as illustrated in FIGS. 1 and 2, the pouch 10 includes an opening 36 to receive a body part or surgical instrument. In the preferred embodiment of the invention, this opening 36 is formed by sealing a sheet of an elastomeric material 38 to the sheet 14 from which the pouch 10 is formed. This phase of manufacture is illustrated in FIG. 3(a). After the elastomeric material 38 has been sealed to sheet 14, a channel 24 is formed.

In the preferred embodiment of the invention, the channel 24 is formed by simply folding the second edge 22 over to form a sleeve 34 as illustrated in FIG. 3(b). The channel material is heat sealed along the second edge 22 to form a continuous channel 24. In other embodiments of the invention, the channel 24 may be located any distance desired away from the second edge 22 as illustrated in FIG. 3(c).

Figure 4:
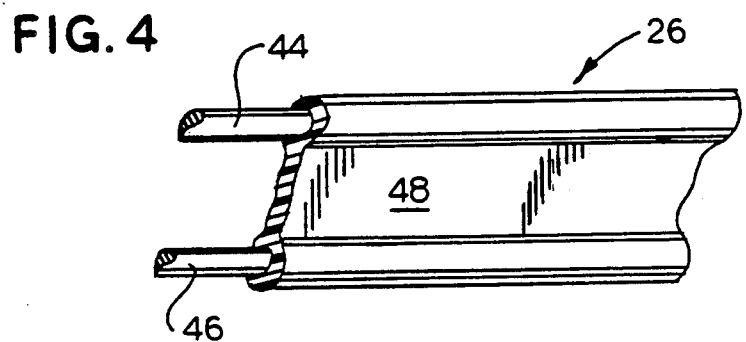
FIG. 4 is an illustration of one embodiment of a drawstring as used in the present invention.

Referring now to FIG. 1 again, in the preferred embodiment of the invention, the drawstring 26 is formed from a malleable and conformable material. For instance, the drawstring may be formed from at least one wire 40 surrounded by a relatively soft flexible protective layer 42. The purpose of the protective layer is to prevent the wire from tearing a hole in sheet 14 of pouch 10. In another embodiment of the invention, the drawstring 26 is formed from at least two wires 44 and 46 that are in parallel juxtaposition with one another. Both wires are surrounded by a protective polymeric coating 48 as illustrated in FIG. 4.

Figure 7A:
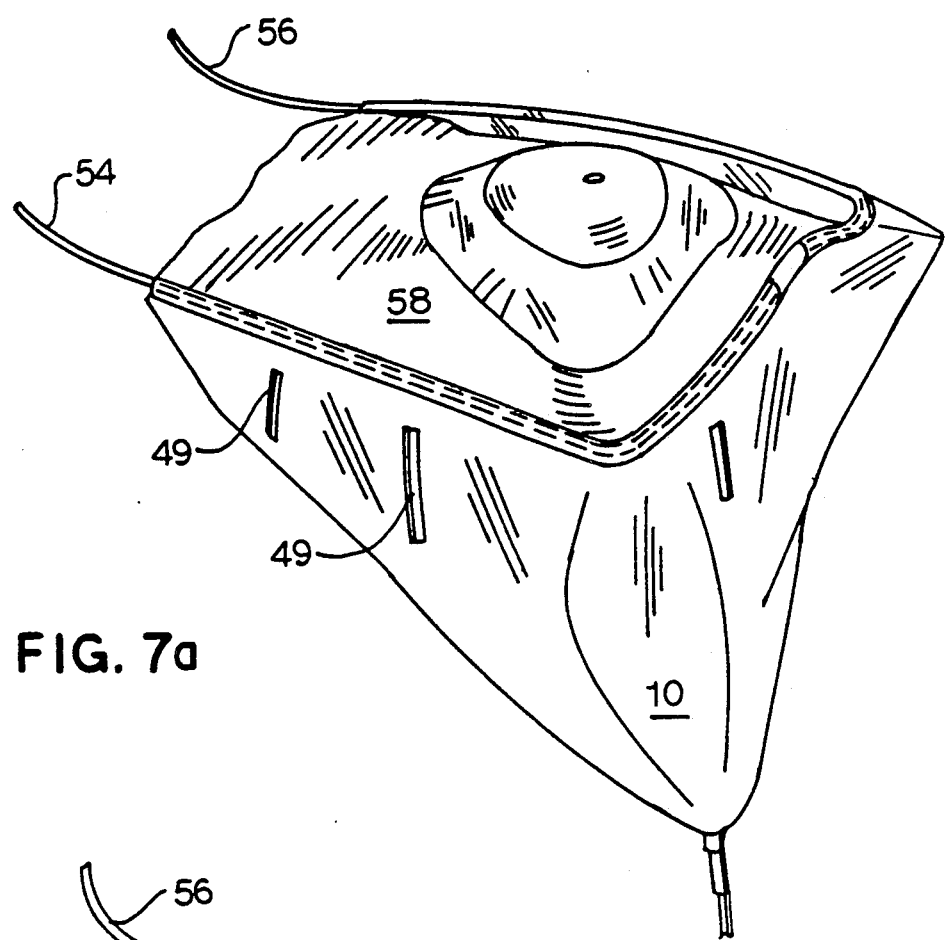
FIGS. 7(a) and (b) illustrates one embodiment of the invention during a caesarean birth procedure.
Figure 7B:
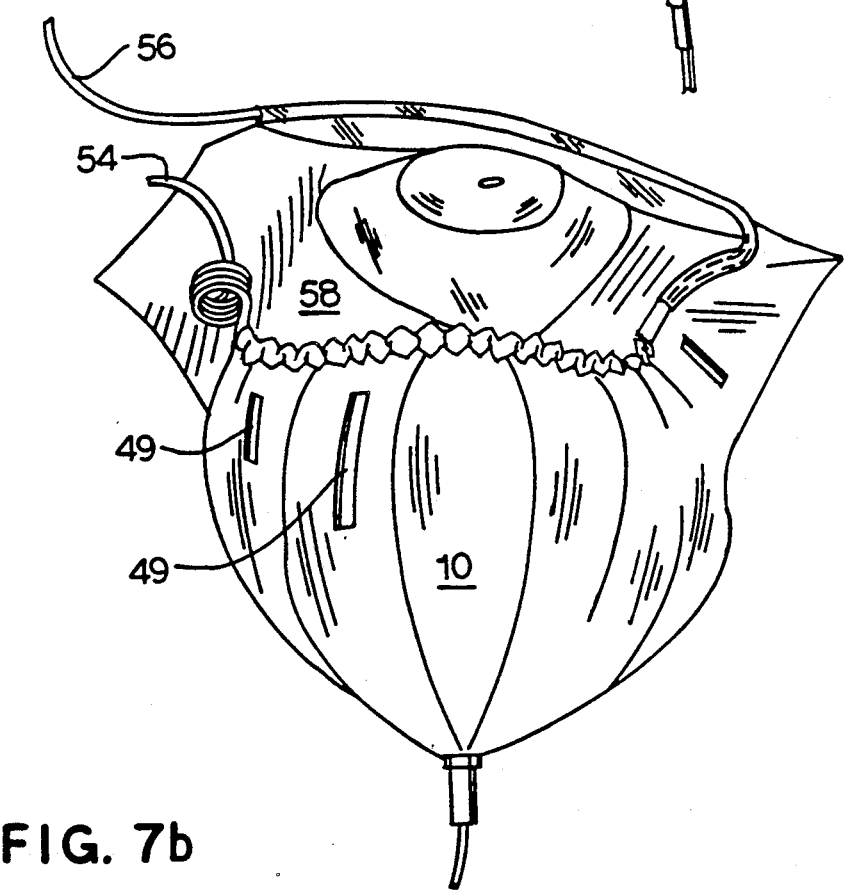

In other embodiments of the invention, the drawstring 26 may be formed from a relatively flexible material. In such embodiments, it is then necessary to have the pouch 10 formed from a relatively rigid material to ensure that the pouch 10 maintains its concave shape after the second edge 22 has been gathered by pulling drawstring 26. In other embodiments it may be desirable to include a malleable bar 49 close to the drawstring to maintain the shape of the pouch as illustrated in FIG. 7(a) and (b).

Figure 5:
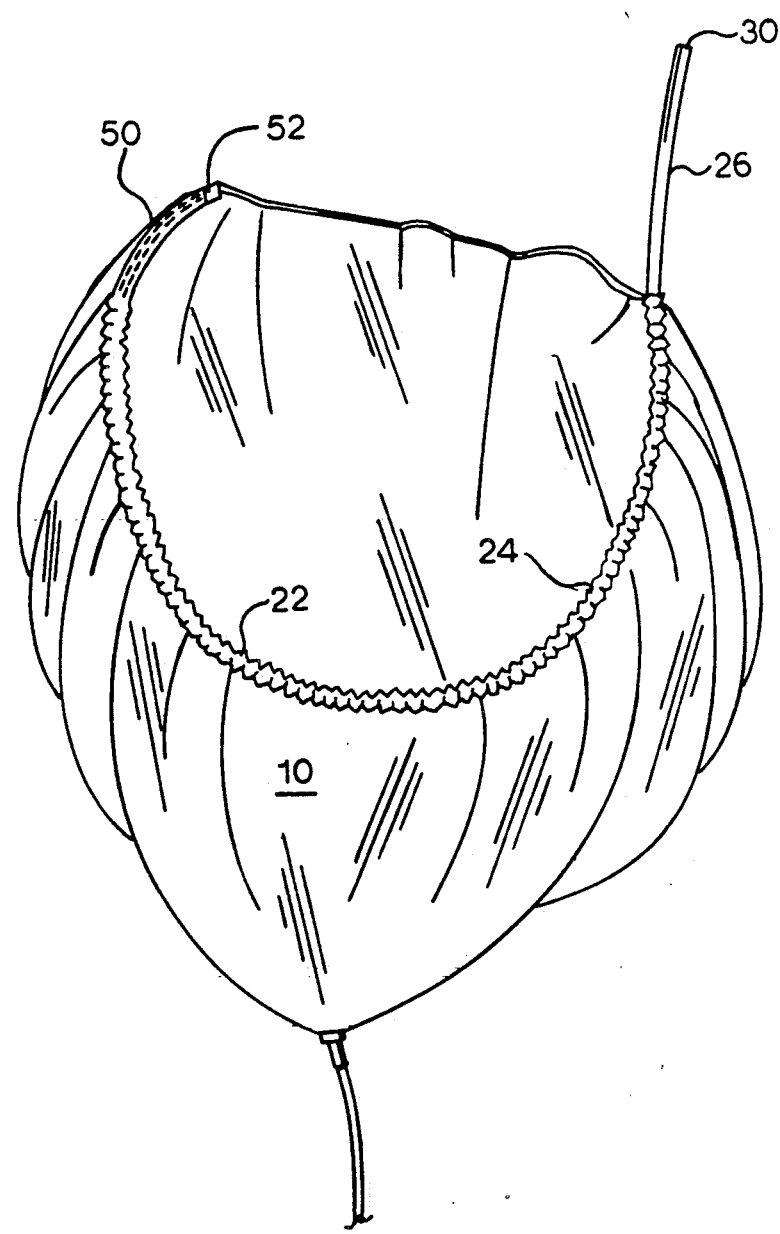
FIG. 5 illustrates another embodiment of the invention in which the a portion of the drawstring is attached to a channel.

In another embodiment of the invention as illustrated in FIG. 5, a portion 50 of the drawstring 26 may be physically attached to the pouch 10. Thus, when end 30 of the drawstring is pulled, the portion of the second edge 22 between the point of attachment 52 and the end of the channel from which end 30 extends will form the concave portion 32 of the pouch 10.

Figure 6:
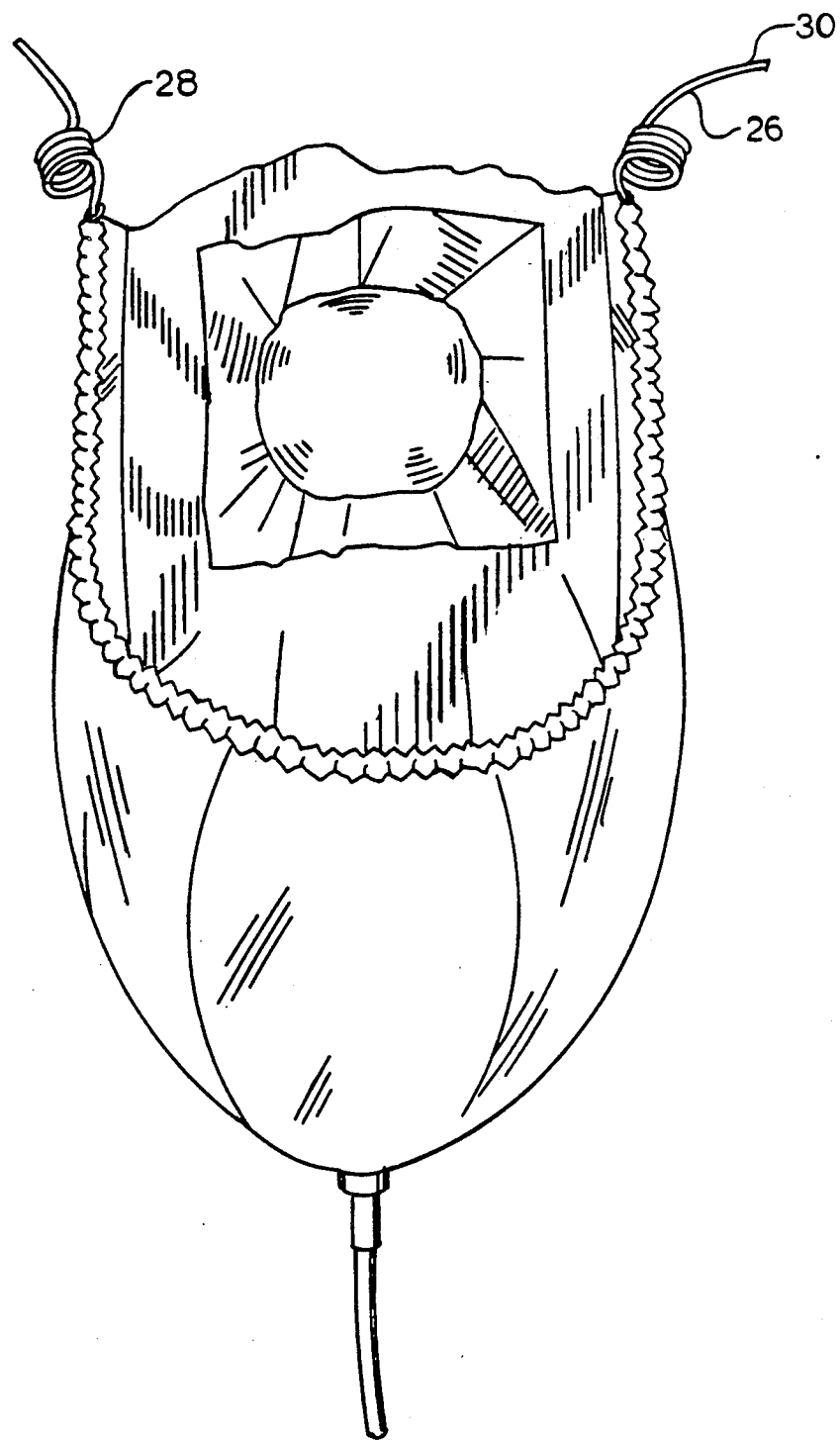
FIG. 6 illustrates one embodiment of the invention for use during a neurosurgical procedure.

While the pouch in the preferred embodiment may be typically used for surgery on a patient's knee as illustrated in FIG. 1, the pouch can be adapted to be used with other drape configurations. For instance, as illustrated in FIG. 6, the pouch can be designed for use during a neurosurgical procedure. In this embodiment of the invention, rather than twisting the ends 28, 30 of the drawstring 26 together, it may be more desirable to simply secure each end 28, 30 to the drape. The ends may be secured by twisting each end separately to prevent each end from retracting into the channel 24 or by other means.

It should be noted that while in some embodiments of the invention it is desirable to have the pouch completely surround the opening at the operative site, in other embodiments of the inventions (such as during a neurological procedure) it may be desirable to have the pouch located about only a portion of the operative site.

In another embodiment of the invention, as illustrated in FIGS. 7(a) and (b), the pouch 10 can be adapted to be used during a caesarean birth procedure. As can be seen in these figures, more than one drawstring may be used. In this particular embodiment, two drawstrings 54 and 56 are used, one being located on each side of the patient's abdomen. Before the drawstrings 54, 56 are pulled, the pouch 10 lays relatively flat against a patient. After each drawstring is pulled, the portion of the pouch on that side of the patient balloons upwardly away from the drape 58.

Figure 8:
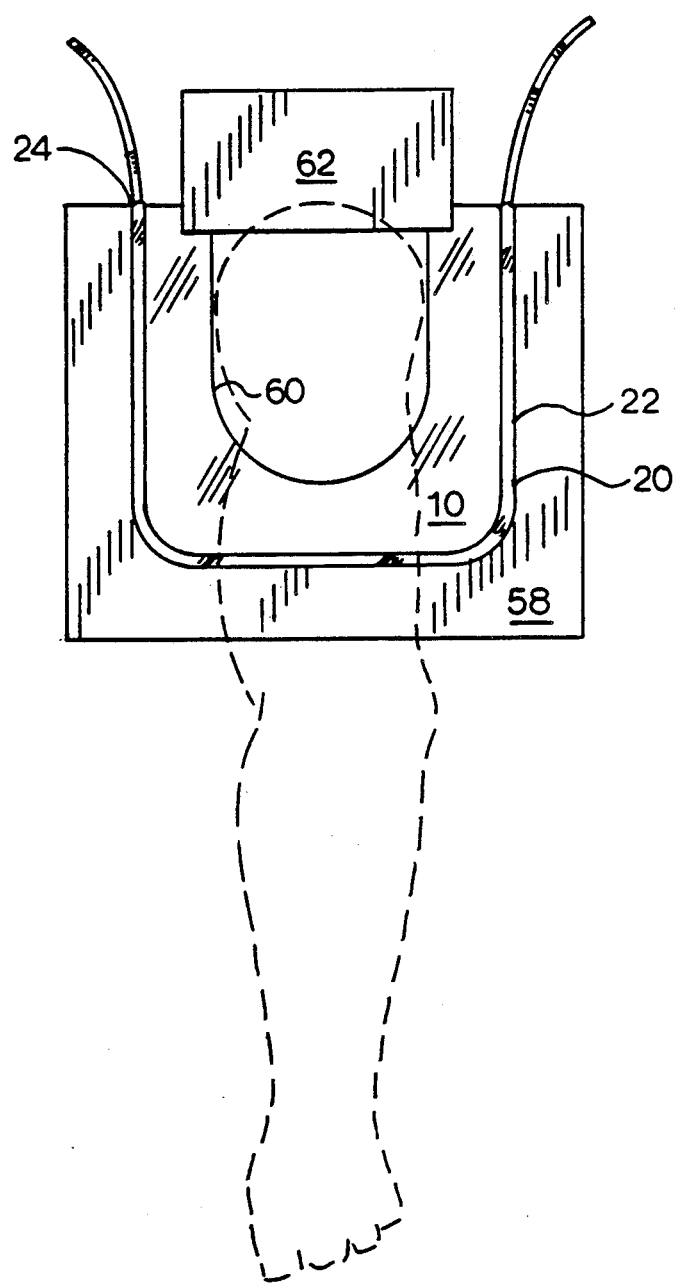
FIG. 8 illustrates another embodiment of the invention for use during an arm or shoulder procedure.

Referring now to FIG. 8, when the subject invention is used for a procedure on a patient's shoulder or arm, a "split sleeve" configuration may be used. In this configuration, a drape 58 may include a U-shaped opening 60. A pouch 10 is attached about so that its second edge 22 surrounds the second opening 60, but is positioned away from the opening so that when a channel 24 disposed along said second edge is gathered, the pouch will form a concave surface 32 about a patient's arm. In the preferred embodiment of the invention, a second drape 62 may be placed above the patient's shoulder to more precisely define the sterile field about the operative site.

It is important to note that the pouch 10 may be attached to a drape 58 using a variety of devices. In many embodiments of the invention, the pouch is physically attached to the drape during the initial manufacture of the drape. In such instances, the pouch may be attached to the drape by use of an adhesive or heat sealing process. In the preferred embodiment, the pouch is attached to the drape using a pressure sensitive adhesive.

In another embodiment of the invention, the pouch 10 is not attached to the drape 58 until the drape has been placed over a patient. The pouch may then be attached to the drape. Generally, the pouch would be attached through the use of one or more strips of pressure sensitive adhesive. In rare instances, it may be desirable to attach the pouch directly to a patient or to a piece of equipment.

In another embodiment of the invention, the pouch 10 may include a opening 63 to drain fluid out of the pouch as illustrated in FIG. 7(a). The pouch 10 may also include an openings to receive a body part or surgical instrument as illustrated in FIG. 1.

Figure 9A:
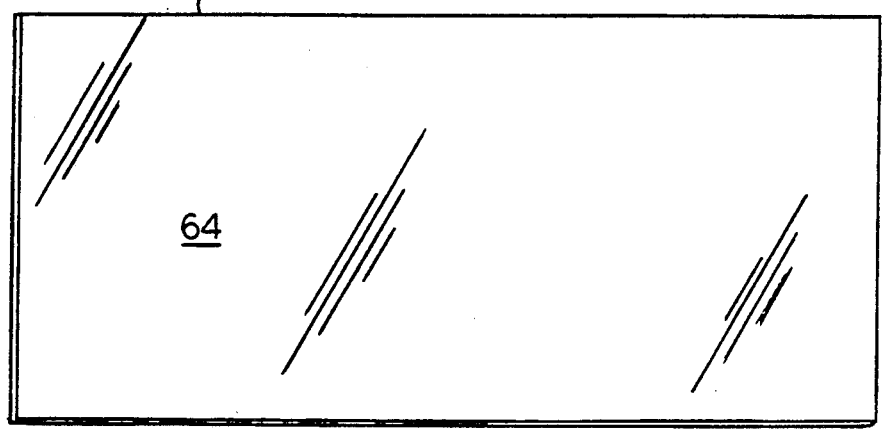
FIG. 9 illustrates some of the manufacturing steps involved in forming a portion of the subject invention.
Figure 9B:
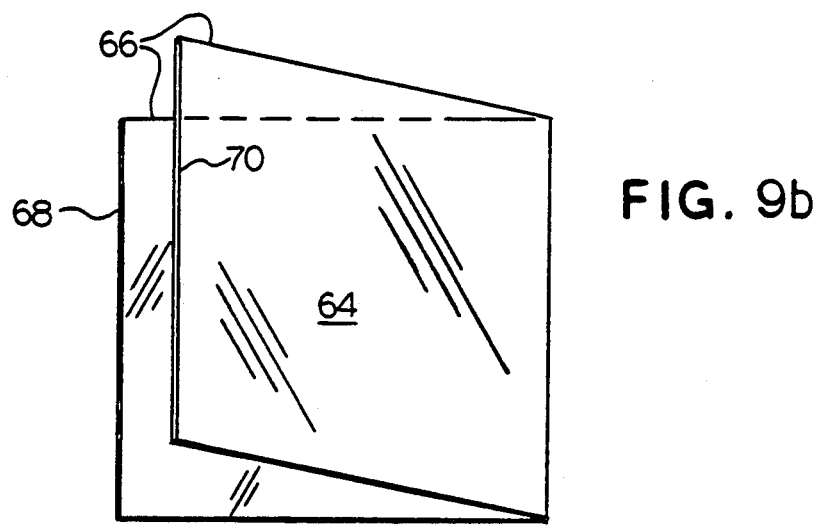
Figure 9C:
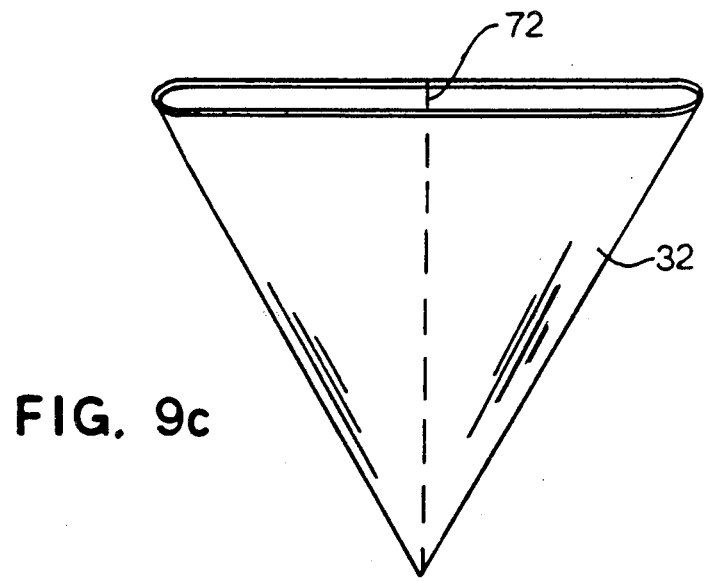

A particularly interesting feature of the preferred embodiment of the subject invention is the technique by which the pouch 10 may be formed from a single elongated rectangular sheet 64, as illustrated in FIGS. 9(a), (b) and (c). In this embodiment as illustrated in FIG. 9(b), one edge 66 is sealed to itself by folding the sheet 64 in half across the width of the sheet to bring opposite ends 68 and 70 of the single edge 66 of the sheet in juxtaposition with each other and sealing these opposite ends of the edge 66 to form a seam 72. This creates a triangular shaped concave surface 32 as illustrated in FIG. 9(c). In the preferred embodiment of the invention, the seam 72 is attached to the drape 58 so that the triangular shaped concave surface 32 stands away from the drape 58 and does not include any seams which could impair a physician's ability to see the operative site or could impair the ability to shape the pouch into the desired configuration.

We claim:

1. A surgical pouch for controlling fluids at a surgical site and containing such fluids comprising:
   at least one sheet formed from a flexible fluid impervious material, said sheet having a front surface, a back surface, a first edge for placement in close proximity to such surgical site, and a second edge located away from said first edge, said second edge having at least one channel extending along at least a portion thereof; and
   a drawstring formed of a malleable and conformable material and further formed of at least one wire surrounded by a relatively soft flexible protective layer, said drawstring having first and second ends, said drawstring extending through at least a portion of said channel and having at least one of said ends extending beyond said channel to allow said drawstring to be pulled so as to gather at least a portion of said second edge along said channel to form a generally concave surface to control fluids at such surgical site and contain such fluids.

2. Surgical pouch as recited in claim 1 wherein protective layer is formed from a polymeric material.

3. A surgical pouch as recited in claim 2 wherein protective layer is formed by coating said wire.

4. A surgical pouch as recited in claim 2 wherein said drawstring includes two generally parallel wires having a polymeric coating surrounding said wires.

5. A surgical pouch as recited in claim 1 wherein said first and second ends of said drawstring extend beyond opposite ends of said channel so that said ends can be twisted together after said second edge is gathered to maintain the shape of said concave surface.

6. A surgical pouch as recited in claim 1 wherein including means for securing said drawstring after said second edge is gathered to maintain said concave surface.

7. A surgical drape for controlling fluids at a surgical site and containing such fluids comprising:
   a main layer of material having a front surface, a back surface, a top edge and a bottom edge joined by a pair of opposing side edges, said layer having an opening located therein for placement about a surgical site;
   a pouch formed from at least one sheet of a flexible fluid impervious material, said sheet also having a front surface, a back surface, a first edge and a second edge located away from said first edge, said second edge having at least one channel extending along at least a portion of said second edge, said back surface of said sheet of said pouch being attached to said front surface of said main layer of material so that said first edge surrounds at least a portion of said opening; and
   a drawstring formed of a malleable and conformable material and further formed of at least one wire surrounded by a relatively soft flexible protective layer, said drawstring having first and second ends, said drawstring extending through at least a portion of said channel and having at least one of said ends extending beyond said channel to allow said drawstring to be pulled to as to gather at least a portion of said second edge along said channel to form a generally concave surface to control fluids at such surgical site and contain such fluids.

8. A surgical drape as recited in claim 7 wherein said first edge of said pouch completely surrounds said fenestration.

9. A surgical drape as recited in claim 8 wherein said first edge of said pouch is in proximity to said fenestration and said second edge of said pouch is away from said fenestration so that when said second edge is gathered a concave surface forms in said sheet of said pouch, said second edge is positioned away from said layer of material, and said concave surface is below said surgical site.

10. A surgical drape as recited in claim 9 wherein said first and second ends of said drawstring extend beyond the ends of said channel to allow said first and second ends to be pulled to gather said second edge of said sheet of said pouch.

11. A surgical drape as recited in claim 10 wherein first and second ends of said drawstring may be secured to maintain the shape of such concave surface.

12. A surgical drape as recited in claim 9 wherein at least one of said ends of said drawstring extend beyond said channel and said drawstring is securable after said second edge is gathered to maintain said concave surface.

13. A surgical drape as recited in claim 7, wherein at least a portion of said drawstring is fastened to said sheet.

14. A surgical drape as recited in claim 13 wherein said drawstring is fastened to said sheet in a location with said channel.

15. A surgical drape for controlling fluids at a surgical site and containing such fluids comprising:
   a main layer of material having a front surface, a back surface, a top edge and a bottom edge joined by a pair of opposing side edges, said layer having an opening located therein for placement about a surgical site;

a pouch formed from a single sheet of a flexible fluid impervious material having an elongated rectangular shape in which the sheet forms said pouch by folding the sheet in half across the width of said sheet to bring opposite ends of a first single edge of said sheet in juxtaposition with one another and sealing said opposite ends to said single edge to one another to form a seam and to create a triangular shaped concave surface out of said sheet;

a channel formed in said single sheet of said sheet pouch along a second edge opposite said first single edge;

a drawstring having first and second ends, said drawstring extending through at least a portion of said channel and having at least one of said ends extending beyond said channel to allow said drawstring to be pulled to as to gather at least a portion of said second edge along said channel to form a generally concave surface to control fluids at such surgical site and contain such fluids, said pouch being attached to said main layer of material so that said seam is attached to said main layer of material and said triangular shaped surface extends away from said material.

16. A surgical drape as recited in claim 15 wherein said opening consists of a fenestration within said main layer of material and said seam of said pouch is placed over said fenestration and said sheet forming said pouch includes an orifice therethrough having the same shape and location as said fenestration when said sheet or said pouch is placed on said layer of material.

* * * * *